United States Patent [19]

O'Neil et al.

[11] Patent Number: 5,076,948
[45] Date of Patent: Dec. 31, 1991

[54] LUBRICANT COMPOSITION STABILIZED WITH SUBSTITUTED 1,2,4-TRIAZOLES

[75] Inventors: Robert M. O'Neil, Flixton; Geoffrey Graham, Cheadle Hulme, both of England

[73] Assignee: CIBA-GEIGY Corporation, Ardsley, N.Y.

[21] Appl. No.: 485,916

[22] Filed: Feb. 27, 1990

[30] Foreign Application Priority Data

Mar. 2, 1989 [GB] United Kingdom ............... 8904760
May 9, 1989 [GB] United Kingdom ............... 8910631

[51] Int. Cl.$^5$ .......................................... C10M 133/42
[52] U.S. Cl. .............................................. 252/51.5 R
[58] Field of Search ................................. 252/51.5 R

[56] References Cited

FOREIGN PATENT DOCUMENTS 1563199  3/1980  United Kingdom .

OTHER PUBLICATIONS

A. M. Belousor, et al., Zh. Org. Khim., 16, 2622 (1980).
P. Ballesteros et al., Tetrahedron, 41, 5955 (1985).
U. F. Dallacker et al., Chem. Zeitung, 110, 101 (1986).
C. G. Kruse et al., Recl. Yrav. Chim. Pays-Bas, 98, 371 (1979).

*Primary Examiner*—Prince E. Willis
*Assistant Examiner*—Maria Nuzzolillo
*Attorney, Agent, or Firm*—Luther A. R. Hall

[57] ABSTRACT

The present invention provides compositions comprising organic material susceptible to degradation and, as metal deactivator and/or antioxidant, at least one compound having the formula(I):

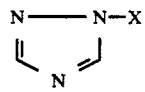

I wherein X is a group of formula II:

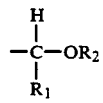

II of formula III:

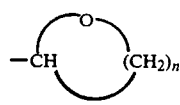

III wherein $R_1$ is $C_1$–$C_{20}$ linear or branched alkyl; $C_5$–$C_{12}$ cycloalkyl; benzyl; or phenyl optionally substituted by halogen, $C_1$–$C_4$ alkyl, $C_1$–$C_4$ alkoxy or nitro; $R_2$ is $C_1$–$C_{20}$ linear or branched chain alkyl, $C_2$–$C_{20}$ linear or branched chain alkyl interrupted by one or more oxygen atoms; $C_5$–$C_{12}$ cycloalkyl; benzyl; or phenyl optionally substituted by halogen, $C_1$–$C_4$ alkyl, $C_1$–$C_4$ alkoxy or nitro; and n is 3 or 4.

8 Claims, No Drawings

LUBRICANT COMPOSITION STABILIZED WITH SUBSTITUTED 1,2,4-TRIAZOLES

The present invention relates to organic material in particular to organic material such as mineral oils containing as metal deactivator and/or antioxidant 1,2,4-triazole compounds.

According to the present invention there are provided compositions comprising organic material and, as metal deactivator and/or antioxidant, at least one compound having the formula (I):

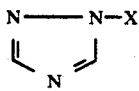

wherein X is a group of formula II:

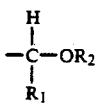

or formula III:

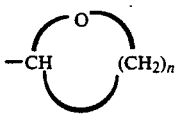

wherein X 1 is $C_1$–$C_{20}$ linear or branched alkyl; $C_5$–$C_{12}$ cycloalkyl; benzyl; phenyl or phenyl which is substituted by halogen, $C_1$–$C_4$ alkyl, $C_1$–$C_4$ alkoxy or nitro; $R_2$ is $C_1$–$C_{20}$ linear or branched alkyl, $C_2$–$C_{20}$ linear or branched alkyl which is interrupted by one or more oxygen atoms; $C_5$–$C_{12}$ cycloalkyl; benzyl; phenyl or phenyl which is substituted by halogen, $C_1$–$C_4$ alkyl, $C_1$–$C_4$ alkoxy or nitro; and n is 3 or 4.

Preferred are compositions as described above, wherein $R_1$ is $C_1$–$C_{12}$ alkyl, $C_5$–$C_7$ cycloalkyl, benzyl, phenyl or phenyl substituted by $C_1$–$C_4$ alkyl and $R_2$ is $C_1$–$C_{12}$ alkyl, $C_5$–$C_7$ cycloalkyl, benzyl, phenyl or phenyl substituted by $C_1$–$C_4$ alkyl. Especially preferred for $R_2$ is $C_1$–$C_{12}$ alkyl, $C_5$–$C_7$ cycloalkyl or benzyl.

Especially preferred are compositions as described above, wherein $R_1$ is $C_1$–$C_6$ alkyl, phenyl, phenyl which is substituted by —$CH_3$ or —$OCH_3$ and $R_2$ is $C_4$–$C_6$ alkyl, $C_5$ alkyl which is interrupted by two oxygen atoms; or is cyclohexyl.

When $R_1$ or $R_2$ is $C_1$–$C_{20}$ linear or branched alkyl, examples include methyl, ethyl, n-propyl, isopropyl, n-butyl, sec-butyl, t-butyl, n-pentyl, n-hexyl, n-octyl, n-decyl, n-dodecyl, n-tetradecyl, n-hexadecyl, n-octadecyl and n-eicosyl.

$C_2$–$C_{20}$ Linear or branched alkyl groups $R_2$ interrupted by one or more oxygen atoms include, e.g. methoxymethyl, ethoxymethyl, 2-methoxyethyl, 2-ethoxyethyl, 3-methoxypropyl, 1- or 2-methoxybutyl and ethoxyoctadecyl or a group of formula —$CH_2$—$CH_2$—O—$CH_2$—$CH_2$—O—$CH_3$.

$C_5$–$C_{12}$ Cycloalkyl groups $R_1$ or $R_2$ are, e.g. cyclopentyl, cyclohexyl, cyclooctyl, cyclodecyl and cyclododecyl, preferred is cyclohexyl.

Optionally substituted phenyl groups $R_1$ or $R_2$ include phenyl, chlorophenyl, bromophenyl, methyl-, ethyl-, n-propyl- and n-butylphenyl, methoxy-, ethoxy-, n-propoxy- and n-butoxyphenyl and nitrophenyl, preferred are phenyl, p-$C_1$–$C_4$ alkylphenyl, e.g. p-methylphenyl and p-$C_1$–$C_4$ alkoxyphenyl e.g. p-methoxyphenyl.

Preferred for X are groups of formula III as described above, wherein n is 3 and especially preferred wherein n is 4.

The compounds of formula I are known compounds and may be synthesized by known methods.

The compounds of formula I in which X is a group of formula II, viz. compounds having the formula IA:

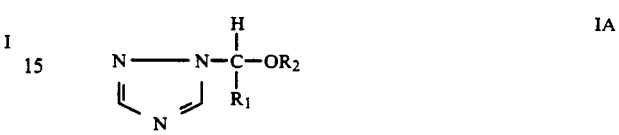

wherein $R_1$ and $R_2$ have their previous significance, may be prepared by a method described in GB Patent Specification No. 1563199. In this reference, compounds of formula IA are produced by reacting 1,2,4-triazole with a halo-ether hal-$CH(R_1)$—$OR_2$ in which $R_1$ and $R_2$ have their previous significance and hal denotes halogen, especially bromine or chlorine.

While GB No. 1563199 discloses the compounds of formula IA and their production, GB No. 1563199 describes merely the pesticidal action of the compounds of formula IA. Their use as metal deactivators and/or antioxidants in organic materials is not suggested.

One particular compound of formula IA may also be prepared by the method disclosed by A. M. Belousov et al., Zh. Org. Khim. 1980, 16, 2622-3, by reacting 1,2,4-triazole with butylvinyl ether, in dichloroethane, in the presence of orthophosphoric acid. Likewise, another specific compound of formula IA may be prepared by the method of Ballesteros et. al. Tetrahedron, 1985, 41, 5955-5963 by reacting 1,2,4-triazole with benzaldehyde dimethylacetal, in hexane or toluene, using p-toluene sulphonic acid, as catalyst.

Neither Belousov et al. nor Ballesteros et al. suggest the use of their specific compounds of formula IA as metal deactivators and/or antioxidants in organic material.

The compounds of formula I in which X is a group of formula II, viz. compounds having the formula IB:

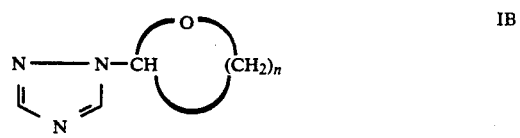

in which n is 3 or 4, may be produced by the method of Dallacker and Minn, Chemiker Zeitung 1986, 110, 101-8 by reacting 1,2,4-triazole with 2,3-dihydrofuran or 3,4-dihydro-2H-pyran, respectively. A compound of formula IB in which n is 3 may also be prepared by reacting 1,2,4-triazole with 2-chlorotetrahydrofuran in the presence of triethylamine, using the method of van der Gen et al., Recl. Trav. Chim, Pays-Bas, 1979, 98, 371-380.

The compounds of formula IA may also be prepared by a new process, which forms a further aspect of the present invention, comprising condensing 1,2,4-triazole with an aldehyde of formula IV $$R_1-CHO \quad IV$$

wherein $R_1$ has its previous significance, and with an alcohol of formula V:

$$R_2-OH \quad V$$

in which $R_2$ has its previous significance.

Preferred is a process as described above wherein $R_1$ is $C_1-C_6$ alkyl, phenyl, phenyl which is substituted by $-CH_3$ or $-OCH_3$ and $R_2$ is $C_4-C_6$ alkyl, $C_5$ alkyl which is interrupted by two oxygen atoms or is cyclohexyl.

The process of the invention is conveniently performed in an inert solvent, in the presence of a catalyst, at an elevated temperature. Examples of inert solvents include aromatic hydrocarbons, e.g. benzene, toluene, xylene, 1,2,4-trimethylbenzene, mesitylene and cumene. Convenient catalysts sulphuric acid, phosphoric acid, acid ion-exchange resins e.g. Amberlyst 15, acid clays e.g. bentonite, montmorillonite and Fullers' Earth and, especially p-toluene sulphonic acid. The reaction is preferably performed with simultaneous removal of water formed in the reaction e.g. by azeotropic removal.

Examples of aldehyde reactants of formula IV include e.g. acetaldehyde, propionaldehyde, isobutyraldehyde, n-pentaldehyde, benzaldehyde, 4-methylbenzaldehyde and 4-methoxybenzaldehyde. Alcohol reactants of formula V include, e.g., methanol, ethanol, n-propanol, isopropanol, n-butanol, n-hexanol, 2-(methoxyethoxy)ethanol, and cyclohexanol.

The organic material component of the compositions of the present invention may be any organic material which is susceptible to degradation in the presence of degradants such as metals e.g. iron or copper and/or oxygen. Examples of such organic materials are mineral oils, synthetic oils, fuels, plastics and other polymers.

Of particular interest are lubricants which are of mineral oil origin or are synthetic oils e.g. carboxylic acid esters, especially those intended for use at temperatures at or above 200° C.

Examples of carboxylic acid ester synthetic lubricants include those based on a diester of a dibasic acid and a monohydric alcohol e.g. dioctyl sebacate or dinonyl adipate; or a triester of trimethylol propane and a monobasic acid or mixture of such acids e.g. trimethylol propane tripelargonate, trimethylol propane tricaprylate or mixtures of these; on a tetraester of pentaerythritol and a monobasic acid or a mixture of such acids e.g. pentaerythritol tetracaprylate; or on complex esters derived from monobasic acids, dibasic acids and polyhydric alcohols e.g. a complex ester derived from trimethylolpropane, caprylic acid and sebacic acid; or mixtures of one or more of such carboxylic acid esters.

Other synthetic lubricant bases are those described e.g. in "Schmiermittel-Taschenbuch" (Huethig Verlag, Heidelberg 1974), e.g. phosphates, glycols, polyglycols, polyalkylene glycols and poly-alpha olefins.

Mineral oil-based lubricant bases are preferred.

Fuels may be the known hydrocarbons and mixtures thereof, for example for the use in internal combustion engines, and may be petrols, gasolines, diesel fuels and the like.

The compositions of the present invention preferably contain 0.001 to 5.0%, more preferably 0.02 to 1.0% by weight of a compound of formula I, based on the weight of the organic material.

In addition to the compound of formula I, the lubricant compositions according to the present invention may contain, in order to improve the operating properties of the lubricant, further additives. Such further additives include e.g. further antioxidants e.g. phenolic antioxidants, amine antioxidants, or other antioxidants, further metal deactivators, rust inhibitors, viscosity-index improvers, pour-point depressants, dispersants/surfactants, and anti-wear additives.

The compounds of formula I, when used alone, exert an excellent metal deactivating effect on working metal surfaces e.g. engine parts, especially of iron or, in particular copper, in contact with an organic material containing a metal degradant such as sulphur.

When, however, the organic material per se is the primary target for degradation e.g. when used in the presence of adventitious traces of metals such as iron or copper, and/or oxygen and/or hydroperoxides, then it is very much preferred to use the compound of formula I in combination with a further antioxidant.

Examples of phenolic antioxidants

1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-di-methylphenol, 2,6-di-octadecyl-4-methylphenol, 2,4,6-tricyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butylhydroquinone, 2,5-di-tert-amyl-hydroquinone, 2,6-diphenyl-4-octadecyloxyphenol.

3. Hydroxylated Thiodiphenylethers 2,2'-Thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)-phenol), 2,2'-methylene-bis-(4-methyl-6-cyclo-hexylphenol), 2,2'-methylene-bis-(6-nonyl-4-methylphenol), 2,2'-methylene-bis-(4,6-di-tert-butyl-phenol), 2,2'-ethylidene-bis-(4,6-di-tert-butylphenol), 2,2'-ethylidene-bis-(6-tert-butyl-4- or -5-isobutylphenol), 2,2'-methylene-bis-(6-α-methylbenzyl-4-nonylphenol), 2,2'-methylene-bis-(6-(α,α-dimethylbenzyl)-4-nonylphenol), 4,4'-methylene-bis-(2,6-di-tert-butylphenol), 4,4'-methylene-bis-(6-tert-butyl-2-methylphenol), 1,1'-bis-(5-tert-butyl-4-hydroxy-2-methylphenol)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecyl)-mercapto-butane, ethyleneglycol-bis-[3,3-bis-(3'-tert-butyl-4'-hydroxyphenyl)-butyrate], bis-(3-tert-butyl-4-hydroxy-5-methylphenyl)-dicyclo-pentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethylbenzene, bis-(3,5-di-tert-butyl-4-hydroxybenzyl)-sulfide, 3,5-di-tert-butyl-4-hydroxybenzyl-mercaptoacetic acid-isooctyl-ester, bis-(4-tert-butyl-3-hydroxy-2,6-dimethylbenzyl)-dithiolterephthalate, 1,3,5-tris-(3,5- di-tert-butyl-4-hydroxy-benzyl)-isocyanurate, 1,3,5-tris-(4-tert-butyl-3-hydroxy-2,6-dimethylbenzyl)-isocyanurate, 3,5-di-tert-butyl-4-hydroxy-benzyl-phosphonic acid-dioctadecylester, 3,5-di-tert-butyl-4-hydroxy-benzyl-phosphonic acid-monoethylester, calcium-salt.

6. Acylaminophenols

4-Hydroxy-lauric acid anilide, 4-hydroxy-stearic acid anilide, 2,4-bis-octyl-mercapto-6-(3,5-di-tert-butyl-4-hydroxy-anilino)-s-triazine, N-(3,5-di-tert-butyl-4-hydroxyphenyl)-carbamic acid octyl ester.

7. Esters of β-(3,5-Di-tert-butyl-4-hydroxyphenol)-propionic acid

With mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, bis-hydroxyethyl-oxalic acid diamide.

8. Esters of β-(5-tert-butyl-4-hydroxy-3-methylphenyl)-propionic acid

With mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylenediamine, N,N'-bis-(3,5-di-tert-butyl-4-hydroxyphenyl-propionyl)-trimethylene-diamine, N,N'-bis-(3,5-di-tert-butyl-4-hydroxyphenylpropionyl)-hydrazine.

Examples of amine antioxidants

N,N'-Di-isopropyl-p-phenylenediamine, N,N'-di-sec.-butyl-p-phenylenediamine, N,N'-bis(1,4-dimethylpentyl)-p-phenylene-diamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethyl-butyl)-N'-phenyl-p-phenylene-diamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthyl-amine, octylated diphenylamine, e.g. p,p'-di-tert-octyldi-phenylamine, 4-n-butylaminophenol, 4-butyrylaminophenol, 4-nonanoylaminophenol, 4-dodecanoylamino-phenol, 4-octadecanoyl-aminophenol, di-(4-methoxy-phenyl)-amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di-(phenylamino)-ethane, 1,2-di-[2-methyl-phenyl)amino]-ethane, 1,3-di-(phenylamino)-propane, (o-tolyl)-biguanide, di-[4-(1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, n-allyl-phenothiazine.

Examples for other antioxidants

Aliphatic or aromatic phosphites, esters of thiodipropionic acid or of thiodiacetic acid, or salts of dithiocarbamic or dithiophosphoric acid.

Examples of metal deactivators, for example for copper, are

Triazoles, benzotriazoles and derivatives thereof, tolutriazole and derivatives thereof, 2-mercaptobenzothiazole, 2,5-dimercaptothiadiazole, 5,5'-methylene-bis-benzotriazole, 4,5,6,7-tetrahydro-benzotriazole, salicylidene-propylenediamine and salicylamino-guanidine and salts thereof.

Examples of rust inhibitors are (a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amides, 4-nonyl-phenoxy-acetic acid.

(b) Nitrogen-containing compounds, e.g. I Primary, secondary or tertiary aliphatic or cyclo-aliphatic amines and amine-salts of organic and inorganic acids, e.g. oil-soluble alkylammonium carboxylates II Heterocyclic compounds, e.g. substituted imidazolines and oxazolines.

(c) Phosphorus-containing compounds, e.g. Amine salts of phosphonic acid or phosphoric acid partial esters, zinc dialkyldithio phosphates.

(d) Sulphur-containing compounds, e.g. Barium-dinonylnaphthalene-n-sulphonates, calcium petroleum sulphonates.

Examples of viscosity-index improvers are

Polyacrylates, polymethacrylates, vinylpyrrolidone/methacrylate-co-polymers, polyvinylpyrrolidones, polybutenes, olefin-copolymers, styrene/acrylate-copolymers, polyethers.

Examples of pour-point depressants are

Polymethacrylates, alkylated naphthalene derivatives.

Examples of dispersants/surfactants are

Polybutenylsuccinic acid-amides or -imides, polybutenyl-phosphonic acid derivatives, basic magnesium-, calcium-, and barium-sulfonates and -phenolates.

Examples of anti-wear additives are

Sulphur- and/or phosphorus- and/or halogen-containing compounds e.g. sulphurised vegetable oils, zinc dialkyldithiophosphates, tritolyl-phosphate, chlorinated paraffins, alkyl- and aryldi- and tri-sulphides, triphenyl-phosphorothionate, diethanolamino-methyl-tolutriazole, di(2-ethylhexyl)-aminomethyltolutriazole.

When the organic material is an organic material liable to degradation by oxidation, e.g. a lubricant composition, one particular preferred class of co-additives for use in conjunction with the compounds of formula I, comprises phenolic or amine-type antioxidants, especially amine-type antioxidants e.g. diphenylamine, octylated diphenylamine, N-phenyl-1-naphthylamine and N-(octylated-phenyl)-1-naphthylamine, with which the compounds of formula I exhibit a synergistic effect.

The following Examples further illustrate the present invention.

1. Synthesis of test compounds

The test compounds were synthesized by one of two methods, namely Method A, which is a known method involving the reaction of 1,2,4-triazole with an ether (c.f. Dallacker et al. and Belousov et al., supra); or the method (method B) according to the process of the present invention involving the condensation of 1,2,4-triazole with an aldehyde of formula IV and an alcohol of formula V.

The respective general procedures are:

Method A 1,2,4-triazole (13.8 g; 0.2 mole) is suspended in toluene (200 ml) and the appropriate vinyl ether (0.2 mole) together with para-toluenesulphonic acid (0.7 g) are added. The mixture is then heated to reflux and maintained at reflux for 3 hours. The mixture is cooled to ambient temperature, washed with dilute sodium carbonate solution, then with water and finally dried over anhydrous magnesium sulphate. The dried extract is filtered and the filtrate evaporated on a rotary evaporator. The crude product thus obtained is purified by vacuum distillation.

Method B 1,2,4-triazole (6.9 g; 0.1 mole) is suspended in toluene (300 ml) and the appropriate aldehyde $R_1CHO$ (0.1 mole) and alcohol, $R_2OH$ (0.1 mole) together with para-toluene-sulphonic acid (0.7 g) are added. The mixture is then heated under reflux with azeotropic removal of the water formed in the reaction. After heating for 10 hours under reflux, the mixture is cooled to ambient temperature and the product is isolated by the same work-up procedure as described in Method A.

Using one of methods A or B, the test compounds, indicated in the following Table, are prepared.

| Test Compound | X | Preparative Method | Yield | bp °C. |
|---|---|---|---|---|
| 1 | —CH(OC$_4$H$_9$)—C$_6$H$_5$ | B | 59% | 140°/0.12 mbar |
| 2 | —CH(OC$_4$H$_9$)—C$_6$H$_4$—CH$_3$ (para) | B | 63% | 140°/0.06 mbar |
| 3 | —CH(O-cyclohexyl)—C$_6$H$_5$ | B | 58% | 150°/0.07 mbar |
| 4 | —CH(OC$_4$H$_9$)—C$_6$H$_4$—OCH$_3$ (para) | B | 38% | 140°/0.03 mbar |
| 5 | —CH(OC$_6$H$_{13}$)—C$_6$H$_5$ | B | 66% | 140°/0.03 mbar |
| 6 | —C(H)(OC$_4$H$_9$)(C$_3$H$_7$) | B | 71% | 80°/0.01 mbar |

-continued

| Test Compound | X | Preparative Method | Yield | bp °C. |
|---|---|---|---|---|
| 7 | −CH(OC$_4$H$_9$)−CH(CH$_3$)$_2$ | B | 61% | 90°/0.05 mbar |
| 8 | −CH(C$_3$H$_7$)−O−cyclohexyl | B | 77% | 110°/0.05 mbar |
| 9 | −CH(OC$_4$H$_9$)−C$_6$H$_{13}$ | B | 72% | 130°/0.05 mbar |
| 10 | −CH(C$_3$H$_7$)−(OCH$_2$CH$_2$)$_2$OCH$_3$ | B | 38% | 130°/0.01 mbar |
| 11 | −CH(OC$_4$H$_9$)−CH$_3$ | A | 73% | 105°/0.01 mbar |
| 12 | −CH(tetrahydropyranyl-O) | A | 39% | 100°/0.05 mbar |
| 13 | −CH(tetrahydrofuranyl-O) | A | 41% | 90°/0.05 mbar |
| 14 | −CH(O-(2-ethylhexyl))−CH$_3$ | A | 45% | 100°/0.08 mbar |
| 15 | −CH(CH$_3$)−O−cyclohexyl | A | 87% | 140°/0.3 mbar |

EXAMPLES 1 TO 5

(Modified) ASTM D-130 Copper Strip Test

A 0.05% or 0.10% solution of the test compound is prepared in a turbine quality mineral oil of viscosity 26.2 mm$^2$/s at 40° C., 4.8 mm$^2$/s at 100° C. and S-content of 0.54% in which 50 ppm of elemental sulphur has been dissolved.

A copper strip (60×10×1 mm) is polished with 100 grade silicon carbide grit which has been picked up on cotton wool wetted with petroleum ether. The polished strip is then immediately totally immersed in the prepared solution, which is maintained at 100° C. for 2 hours. After this time, the strip is removed, washed with petroleum ether, dried and its colour is compared with those of the ASTM D-130 Copper Strip Corrosion Standard Chart. The results are summarised in the following Table:

| | Modified ASTM D-130 Copper Strip Test | | |
|---|---|---|---|
| Example | Test compound No. | Concentration | ASTM D-130 Rating |
| — | Blank (no additive) | — | 3B |
| 1 | 1 | 0.10% | 1B |
| 2 | 2 | 0.05% | 1B |
| 3 | 3 | 0.10% | 1B |
| 4 | 4 | 0.10% | 1A |
| 5 | 5 | 0.10% | 1B |

A rating of 1 denotes a slight tarnish; a rating of 2 a moderate tarnish; a rating of 3 a dark tarnish; and a rating of 4 severe corrosion. Letters A, B, C and D are used to indicate shadings within the broad numerical values.

The results in the Table demonstrate the excellent test results achieved using compositions according to the present invention.

EXAMPLES 6 TO 46

Rotary Bomb Oxidation Test ASTM D-2272

A 0.05% solution of the test compound is prepared in a turbine quality mineral oil of viscosity 26.2 mm²/s at 40° C., 4.8 mm²/s at 100° C. and S-content of 0.54% which may also contain either a phenolic or aminic antioxidant, or both.

The time taken for the oxygen pressure in the bomb to drop more than 175 kPa below the maximum pressure is recorded.

The results obtained are set out in the following Table:

| | | ASTM D-2272 Rotary Bomb Oxidation Test | | | |
|---|---|---|---|---|---|
| Example | Test Compound No. | Antioxidant Q | Antioxidant R | Antioxidant S | RBOT mins to 175 kPa pressure drop |
| | Base Oil Alone | — | — | — | 25 mins |
| — | — | 0.10% | — | — | 65 mins |
| — | — | — | 0.10% | — | 85 mins |
| — | — | — | — | 0.10% | 270 mins |
| 6 | 1 | 0.10% | — | — | 400 mins |
| 7 | 1 | — | 0.10% | — | 1030 mins |
| 8 | 1 | — | — | 0.10% | 1050 mins |
| 9 | 1 | 0.05% | 0.05% | — | 820 mins |
| 10 | 1 | — | — | — | 112 mins |
| 11 | 2 | 0.10% | — | — | 330 mins |
| 12 | 2 | — | 0.10% | — | 850 mins |
| 13 | 3 | 0.10% | — | — | 315 mins |
| 14 | 3 | — | 0.10% | — | 490 mins |
| 15 | 4 | 0.10% | — | — | 340 mins |
| 16 | 4 | — | 0.10% | — | 655 mins |
| 17 | 5 | 0.10% | — | — | 345 mins |
| 18 | 5 | — | 0.10% | — | 565 mins |
| 19 | 6 | 0.10% | — | — | 290 mins |
| 20 | 6 | — | 0.10% | — | 1005 mins |
| 21 | 7 | 0.10% | — | — | 320 mins |
| 22 | 7 | — | 0.10% | — | 900 mins |
| 23 | 8 | 0.10% | — | — | 375 mins |
| 24 | 8 | — | 0.10% | — | 955 mins |
| 25 | 9 | 0.10% | — | — | 220 mins |
| 26 | 9 | — | 0.10% | — | 345 mins |
| 27 | 10 | 0.10% | — | — | 180 mins |
| 28 | 10 | — | 0.10% | — | 200 mins |
| 29 | 11 | 0.10% | — | — | 300 mins |
| 30 | 11 | — | 0.10% | — | 1040 mins |
| 31 | 11 | 0.025% | 0.075% | — | 1000 mins |
| 32 | 11 | 0.05% | 0.05% | — | 875 mins |
| 33 | 11 | 0.075% | 0.025% | — | 640 mins |
| 34 | 11 | — | 0.05% | — | 800 mins |
| 35 | 11 | 0.05% | 0.15% | — | 1070 mins |
| 36 | 11 | 0.10% | 0.10% | — | 1175 mins |
| 37 | 11 | 0.15% | 0.05% | — | 720 mins |
| 38 | 11 | — | — | — | 80 mins |
| 39 | 12 | 0.10% | — | — | 310 mins |
| 40 | 12 | — | 0.10% | — | 970 mins |
| 41 | 13 | 0.10% | — | — | 330 mins |
| 42 | 13 | — | 0.10% | — | 1150 mins |
| 43 | 14 | 0.05% | — | — | 285 mins |
| 44 | 14 | — | 0.05% | — | 300 mins |
| 45 | 15 | 0.05% | — | — | 90 mins |
| 46 | 15 | — | 0.05% | — | 170 mins |

Antioxidant Q is a commercially available mixture of tert-butylated phenols.

Antioxidant R is a commercially available di-tert-octylated diphenylamine.

Antioxidant S is a commercially available tert-octylphenyl-α-naphthylamine.

The results in the Table indicate that when used in combination with a further amine or phenolic antioxidant, the stabilisers of formula I impart synergistic antioxidant properties to the lubricant compositions of the invention.

All percentages and parts are given by weight unless stated otherwise.

What is claimed is:

1. A stabilized composition comprising a lubricant susceptible to degradation caused by metals and/or oxygen and/or hydroperoxides and, as metal deactivator and/or antioxidant, at least one compound having the formula (I):

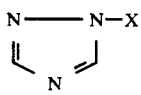

wherein X is a group of formula II:

or formula III:

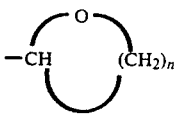

wherein $R_1$ is $C_1$-$C_{20}$ linear or branched alkyl; $C_5$-$C_{12}$ cycloalkyl; benzyl; phenyl or phenyl which is substituted by halogen, $C_1$-$C_4$ alkyl, $C_1$-$C_4$ alkoxy or nitro; $R_2$ is $C_1$-$C_{20}$ linear or branched alkyl, $C_2$-$C_{20}$ linear or branched alkyl which is interrupted by one or more oxygen atoms; $C_5$-$C_{12}$ cycloalkyl; benzyl; phenyl or phenyl which is substituted by halogen, $C_1$-$C_4$ alkyl, $C_1$-$C_4$ alkoxy or nitro; and n is 3 or 4 wherein the composition contains 0.001 to 5.0% by weight of said compound having the formula (I).

2. Composition according to claim 1 wherein the organic material is a mineral oil.

3. Composition according to claim 1 wherein the composition contains 0.01 to 1.0% by weight of the compound of formula I, based on the weight of the lubricant.

4. Composition according to claim 1 wherein the lubricant composition also contains one or more of a further antioxidant, a further metal deactivator, a rust inhibitor, a viscosity-index improver, a pour-point depressant, a dispersant/surfactant and an anti-wear additive.

5. Composition according to claim 4 wherein the further antioxidant is an amine antioxidant.

6. Composition according to claim 5 wherein the amine antioxidant is diphenylamine, octylated diphenylamine, N-phenyl-1-naphthylamine or N-(octylated phenyl)-1-naphthyl-amine.

7. Composition according to claim 6 wherein $R_1$ is $C_1$-$C_{12}$ alkyl, $C_5$-$C_7$ cycloalkyl, benzyl, phenyl or phenyl substituted by $C_1$-$C_4$ alkyl and $R_2$ is $C_1$-$C_{12}$ alkyl, $C_5$-$C_7$ cycloalkyl, benzyl, phenyl or phenyl substituted by $C_1$-$C_4$ alkyl.

8. Composition according to claim 7 wherein $R_1$ is $C_1$-$C_6$ alkyl, phenyl, phenyl which is substituted by —$CH_3$ or —$OCH_3$ and $R_2$ is $C_4$-$C_6$ alkyl, $C_5$ alkyl which is interrupted by two oxygen atoms or is cyclohexyl.

* * * * *